United States Patent [19]

Jäger et al.

[11] E Re. 31,514

[45] Reissued Jan. 31, 1984

[54] PHOTOGRAPHIC MATERIAL CONTAINING A STABILIZER

[75] Inventors: Gerhard Jäger, Leverkusen; Anita von König, Krefeld; Armin Voigt, Cologne; Karl H. Büchel, Burscheid, all of Fed. Rep. of Germany

[73] Assignee: Agfa-Gevaert Aktiengesellschaft, Leverkusen, Fed. Rep. of Germany

[21] Appl. No.: 405,069

[22] Filed: Aug. 4, 1982

Related U.S. Patent Documents

Reissue of:

[64] Patent No.: 4,256,830
Issued: Mar. 17, 1981
Appl. No.: 961,217
Filed: Nov. 16, 1978

[30] Foreign Application Priority Data

Nov. 22, 1977 [DE] Fed. Rep. of Germany ..... 2752046

[51] Int. Cl.[3] ..... G03C 7/26; G03C 7/30; G03C 1/34

[52] U.S. Cl. ..... 430/372; 430/551; 430/607; 430/614

[58] Field of Search ..... 430/372, 551, 607, 614

[56] References Cited

U.S. PATENT DOCUMENTS

| | | | |
|---|---|---|---|
| 3,212,900 | 10/1965 | Oguchi | 96/109 |
| 3,291,607 | 12/1966 | Dersch | 96/22 |
| 3,597,214 | 8/1971 | Mackey et al. | 96/109 |
| 3,615,612 | 10/1971 | Mackey et al. | 96/103 |
| 3,647,439 | 3/1972 | Bass | 96/95 |
| 3,679,423 | 7/1972 | Pollet | 96/109 |
| 3,706,569 | 12/1972 | Gilman et al. | 96/109 |
| 3,772,023 | 11/1973 | Nakajima et al. | 96/109 |
| 4,066,461 | 1/1978 | Shimamura et al. | 96/66.3 |

OTHER PUBLICATIONS

Kuwabara "Effects of Acetylene Derivatives on Photographic Emulsions", Bulletin of the Society of Scientific Photography of Japan, No. 16, Dec. 1966, pp. 13–23.

*Primary Examiner*—Mary F. Downey
*Attorney, Agent, or Firm*—Connolly & Hutz

[57] ABSTRACT

Propyne compounds, which are capable of stabilizing photographic materials against color fog and flattening of the gradation are disclosed. They may be added to emulsion layers and to processing baths.

9 Claims, No Drawings

PHOTOGRAPHIC MATERIAL CONTAINING A STABILIZER

Matter enclosed in heavy brackets [ ] appears in the original patent but forms no part of this reissue specification; matter printed in italics indicates the additions made by reissue.

This invention relates to a photographic material having at least one silver halide emulsion layer which has been improved by the addition of a stabilizer capable of stabilizing the photographic material against the formation of colour fog and flattening of the gradation.

It is known that colour images produced using the usual silver halide containing materials frequently show a colour fog or discolouration. The formation of a colour fog is due, among other things, to the fact that the developer compounds are liable to be oxidized to a certain extent by the atmosphere in which case they will also couple with the colour coupler in those areas of the photographic material in which no silver image has originally been produced. This undesirable oxidation of the developer may be produced not only by the atmosphere but also by additives present in the emulsions. Colour fog and discolouration occur particularly in those photographic materials in which couplers are incorporated in the light sensitive layers.

The use of alkyl and dialkyl hydroquinone derivatives to stabilize against colour fog in colour photographic materials has been proposed in U.S. Pat. Nos. 2,403,721 and 2,701,197 and German Offenlegungsschrift No. 2,110,521.

These compounds have, however, the disadvantage that many of them can only be prepared by a difficult process involving from two to four stages and that some of them are not sufficiently resistant to diffusion so that when used in multilayered photographic materials they are liable to migrate between the individual layers, thereby producing undesirable side effects. Moreover, these compounds partly crystallize during or after their application or have a deleterious effect on the physical or chemical properties of the layers, one particularly disadvantageous effect of some of the alkyl hydroquinones being that they give rise to coloured by-products due to an oxidizing reaction during coating or development. The discolouration of the photographic material caused by these by-products is particularly undesirable in copying materials.

It is also known that colour reproduction can be improved by arranging an intermediate layer between the light sensitive silver halide emulsion layer and a layer containing the colour coupler, to suppress diffusion of the oxidation products of the developers into the layer containing the colour couplers. For this purpose, the intermediate layer contains, inter alia, compounds which react with the developer oxidation products to form colourless compounds. The extent to which the colour fog is reduced by these so called "white couplers" is, however, insufficient for practical purposes.

It has also been disclosed in German Pat. No. 2,304,321 to reduce the discolouration of colour photographic materials by processing them in the presence of 2-propinylthioether derivatives, but even this measure is not sufficiently effective for the increased demands, particularly of high temperature processing.

It is also known that flattening of the gradation is liable to occur in photographic materials in storage particularly if the materials have a relatively steep gradation. From U.S. Pat. No. 3,488,709, it is known that in emulsions which contain rhodium salts to steepen their gradation, this gradation can be stabilized by the addition of cadmium salts. However, it is becoming increasingly accepted as important to avoid the use of cadmium salts in photographic materials if possible.

The need therefore remains for a stabilizer which is capable of stabilizing photographic materials against colour fog and flattening of the gradation.

It is an object of the present invention to provide stabilizers which are capable of stabilizing photographic materials against colour fog and flattening of the gradation. Another object of the invention is to prepare photographic materials containing at least one silver halide emulsion layer, which are stabilized with these compounds.

The invention relates to a photographic material having at least one silver halide emulsion layer and containing at least one stabilizer corresponding to the following formula I or a salt thereof:

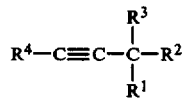

I in which $R^1$ represents an alkyl group, in particular an alkyl group with 1 to 4 carbon atoms; an aryl group in particular a phenyl group, which may be substituted, preferably with halogen or with a nitro, phenyl, phenoxy, alkyl, $CF_3O$ or $CF_3$ group; an aralkyl group or a heterocyclic group, for example pyridyl, in particular pyridyl-(4), pyridyl-(3) or pyridyl-(2);

$R^2$ represents a hydroxyl group or a heterocyclic group, in particular one containing nitrogen and preferably having 5 to 6 ring atoms, for example 1-imidazolyl;

$R^3$ represents an aryl group, in particular phenyl, which may be substituted with one or more substituents, in particular with an alkyl group having one to four carbon atoms or with halogen or a nitro group;

$R^4$ represents hydrogen, alkyl, in particular containing 1 to 5 carbon atoms, dialkylamino alkyl, in particular dimethylamino methyl and diethylamino methyl, morpholino methyl, pyrrolidinyl methyl, aryl, in particularl phenyl, or diphenyl-imidazolylmethyl, provided that at least one of the groups $R^1$ or $R^2$ is a heterocyclic group.

This invention also relates to a process for the production of photographic images by the processing of photographic materials in the presence of the compounds used according to the invention.

The above-mentioned alkyl, aryl and heterocyclic groups may themselves contain substituents which in turn may also be substituted.

By "salts of compounds of formula I" are meant in particular those compounds in which the group $R^2$ is one corresponding to the following general formula and X— is the anion belonging to it:

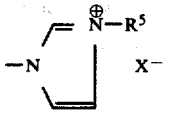

in which $R^5$ represents an alkyl or aralkyl group, in particular a benzyl group or a benzyl group which is substituted by a $C_1$ to $C_4$ alkyl or halogen on the aromatic ring, or hydrogen and $X^{\ominus}$ represents halogen, in particular chlorine, bromine or iodine, or an alkyl sulphate or aryl sulphate anion, in particular a tosyl or mesyl group.

The following compounds of formulae II to IV have proved to be particularly suitable:

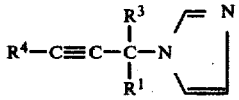

II

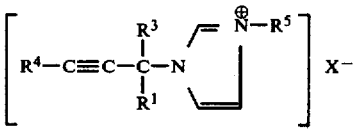

III

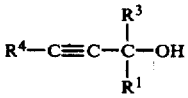

IV in which $R^1$ and $R^4$ have the meanings specified under formula I, $R^3$ represents a phenyl group which may have one or more substituents and $R^5$ and X have the meanings given above.

Examples of compounds which may be used according to the invention are contained in the following Table I to III:

TABLE I

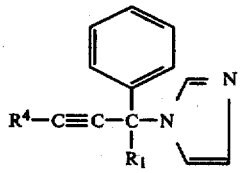

| Compound Number | $R^1$ | $R^4$ | Melting point, boiling point or refractive index |
|---|---|---|---|
| 1 | phenyl | H | m.p.: 134–36° |
| 2 | p-fluorophenyl | H | m.p.: 115–116° |
| 3 | isopropyl | H | b.p.0.05: 160–62° |
| 4 | phenyl | diethylamino-methyl | m.p.: 83–84° |
| 5 | phenyl | N—morpholinomethyl | m.p.: 62.5–64° |
| 6 | m-tolyl | H | m.p.: 86–87° |
| 7 | phenyl | diphenyl-imidazolyl methyl | m.p. 210–11° |
| 8 | isopropyl | phenyl | oil, $n_D^{25}$: 1,6019 |
| 9 | phenyl | N—pyrrolidinyl methyl | m.p.: 66–68° |

TABLE II

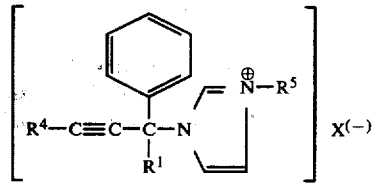

| Compound Number | $R^1$ | $R^4$ | $R^5$ | X | m.p. |
|---|---|---|---|---|---|
| 10 | phenyl | H | benzyl | Cl | 169–70° |
| 11 | phenyl | H | p-methylbenzyl | Cl | 176–77° |
| 12 | phenyl | H | p-chlorobenzyl | Cl | 171–72° |
| 13 | phenyl | H | methyl | I | decomp. 160° |
| 14 | phenyl | H | ethyl | I | 131–32° |

TABLE III

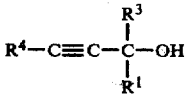

| Compound Number | $R^3$ | $R^1$ | $R^4$ | m.p. |
|---|---|---|---|---|
| 15 | phenyl | 4-pyridyl | H | 165–66° |
| 16 | phenyl | 2-pyridyl | H | 61–62° |
| 17 | p-tolyl | 4-pyridyl | H | 191–93° |
| 18 | phenyl | 3-pyridyl | H | 140–41° |

The compounds which are to be processed according to the invention may be prepared by known methods. The carbinols and imidazole derivatives may be prepared according to German Offenlegungsschrift No. 2,044,621.

The preparation of 1,1-diphenyl-1-[imidazolyl-(1)]-propyne (compound No. 1) will be described by way of example:

Preparation of compound No. 1(1,1-diphenyl-1-[imidazolyl-(1)]-propyne: 7.5 mol of phosphoric acid-tris-imidazolide and 6.73 mol of 1,1-diphenyl propinol are introduced into 5 liters of acetonitrile and heated under reflux for 48 hours. 4 liters of acetonitrile then distilled off at normal pressure within 3 hours and the residue is stirred up in 15 liters of water. The product is extracted with 8.0 liters of methylene chloride, the organic phase is separated off and 7.5 liters of methylene chloride are distilled off. 900 ml of acetonitrile are added to the residue which is then cooled. The crystals which form are separated by suction filtration, suspended in 1 liter of cold acetonitrile, sucked dry and dried in a circulating air dryer at 50° C.

Yield: 750 g (=43% of the theoretical yield) of 1,1-diphenyl-1-[imidazolyl-(1)]-propyne, m.p. 134°–136° C.

Although a photographic material containing silver complexes of certain propinols which are substituted with alkyl or aryl groups has already been disclosed in German Offenlegungsschrift No. 2,159,631, these silver complexes are used in combination with certain sensitizers and are intended to compensate for the loss in sensitivity caused by the addition of the sensitizer, but they cause a marked increase in the fogging of the photographic materials.

The usual silver halide emulsions are suitable for the present invention. The silver halides contained in them may be silver chloride, silver bromide or mixtures thereof, which may have a silver iodide content of up to 10 mol percent.

The materials prepared according to the invention may be developed with the usual colour developer substances, e.g. the following:

N,N-dimethyl-p-phenylene diamine;
4-amino-3-methyl-N-ethyl-N-methoxyethyl aniline;
monoethyl-p-phenylene diamine;
2-amino-5-diethylamino toluene;
N-butyl-N-ω-sulphobutyl-p-phenylene diamine;
2-amino-5-(N-ethyl-N-β-methane sulphonamidoethyl amino)toluene
N-ethyl-N-β-hydroxyethyl-p-phenylene diamine;
N,N-bis-(β-hydroxyethyl)-p-phenylene diamine and
2-amino-5-(N-ethyl-N-β-hydroxyethyl amino)-toluene.

Other suitable colour developers have been described, for example, in J. Amer. Chem. Soc. 73,3100 (1951).

The photographic material prepared according to the invention may contain the usual colour couplers which are generally incorporated in the silver halide layers. The red sensitive layer, for example, contains a non-diffusible colour coupler for producing the cyan partial colour image, generally a coupler based on phenol or α-naphthol. The green sensitive layer contains at least one non-diffusible colour coupler for production of the magenta partial colour image, usually a colour coupler based on 5-pyrazolone or indazolone. The blue sensitive layer unit contains at least one non-diffusible colour coupler for producing the yellow partial colour image, generally a colour coupler having an open chain ketomethylene group. Colour couplers of this type are known in large numbers and have been described in numerous Patent Specifications as well as in other publications, for example in the publication entitled "Farbkuppler" by W. Pelz, in "Mitteilungen aus den Forschungslaboratorien der Agfa, Leverkusen/München" Volume III (1961) and the publication by K. Venkataraman in "The Chemistry of Synthetic Dyes," Volume 4, 341 to 387, Academic Press, 1971.

2-equivalent couplers may also be used as nondiffusible colour couplers. These contain a removable substituent in the coupling position so that they only require two equivalents of silver halide for colour production, in contrast to the usual 4-equivalent couplers. Suitable 2-equivalent couplers include, for example, the known DIR couplers, in which the removable group is released as a diffusible development inhibitor after the reaction with the oxidation products of the colour developers. So-called white couplers may also be used for improving the properties of the photographic material.

The non-diffusible colour couplers and colour producing compounds are added to the light sensitive silver halide emulsions or other casting solutions by the usual known methods. If they are soluble in water or alkalis, they may be added to the emulsions in the form of aqueous solutions to which water miscible organic solvents such as ethanol, acetone or dimethyl formamide may be added. If, on the other hand, the non-diffusible colour couplers and colour producing compounds are insoluble in water and alkalis, they may be emulsified in known manner, for example a solution of the compounds in a low boiling organic solvent may be mixed directly with the silver halide emulsion or it may first be mixed with an aqueous gelatine solution, the organic solvent then being removed in the usual manner. In that case, the resulting emulsion of the given comound in gelatine is then mixed with the silver halide emulsion. In addition, so called coupler solvents or oil formers may be used to emulsify such hydrophobic compounds. These oil formers are generally relatively high boiling organic compounds in which the non-diffusible colour couplers and development inhibitor releasing compounds which are required to be emulsified in the silver halide emulsions become enclosed in the form of oily droplets. Information on this may be found, for example, in U.S. Pat. Nos. 2,322,027; 2,533,514; 3,689,271; 3,764,336 and 3,765,897.

The binder used for the photographic layers is preferably gelatine but this may be partly or completely replaced by other natural or synthetic binders. Suitable natural binders include, for example, alginic acid and its derivatives such as its salts, esters, or amides, cellulose derivatives such as carboxymethyl cellulose, alkyl celluloses, such as hydroxyethyl cellulose, starch or its derivatives such as ethers or esters, or carrageenates. Suitable synthetic binders include polyvinyl alcohol, partially saponified polyvinyl acetate and polyvinyl pyrrolidone.

The emulsions may also be chemically sensitized e.g. by the addition of sulphur compounds such as allyl isothiocyanate, allyl thio urea and sodium thiosulphate at the stage of chemical ripening. Reducing agents may also be used as chemical sensitizers, e.g. the tin compounds described in Belgian Pat. Nos. 493,464 and 568,687, or polyamides such as diethylene triamine or aminomethyl sulphinic acid derivatives, e.g. according to Belgian Pat. No. 547,323.

Noble metals such as gold, platinum, palladium, iridium, ruthenium or rhodium and compounds of these metals are also suitable chemical sensitizers. This method of chemical sensitization has been described in the article by R. Koslowsky, Z. Wiss. Phot. 65–72 (1951).

The emulsions may also be sensitized with polyalkylene oxide derivatives, e.g. with polyethylene oxides having molecular weights of from 1,000 to 20,000 or with condensation products of alkylene oxide and aliphatic alcohols, glycols, cyclic dehydration products of hexitols, alkyl substituted phenols, aliphatic carboxylic acids, aliphatic amines, aliphatic diamines or amides. The condensation products should have a molecular weight of at least 700, preferably more than 1,000. These sensitizers may, of course, be combined in order to produce special effects, as described in Belgian Pat. No. 537,278 and in British Pat. No. 727,982.

The emulsions may also be optionally sensitized e.g. with the usual polymethine dyes such as neutrocyanines, basic or acid carbocyanines, rhodacyanines, hemicyanines, styryl dyes and oxonoles. Sensitizers of this type have been described in the work by F. M. Hamer "The Cyanine Dyes and related Compounds," (1964).

The emulsions may contain the usual stabilizers, e.g. homopolar compounds or salts of mercury containing aromatic or heterocyclic rings, such as mercapto triazoles, or simple mercury salts, sulphonium mercury double salts and other mercury compounds. Azaindenes are also suitable stabilizers, particularly tetra and pentaazaindenes and especially those which are substituted with hydroxyl or amino groups. Compounds of this type have been described in the article by Birr, Z. Wiss Phot. 47 (1952), 2 to 58. Other suitable stabilizers include inter alia heterocyclic mercapto compounds, e.g. phenyl mercapto tetrazole, quaternary benzthiazole derivatives and benzotriazole.

The emulsions may be hardened in the usual manner, for example with formaldehyde or halogen substituted aldehydes which contain a carboxyl group, such as mucobromic acid, diketones, methane sulphonic acid esters and dialdehydes.

The photographic layers may also be hardened with epoxide type hardeners, heterocyclic ethylene imine hardeners or acryloyl hardeners. Examples of such hardeners have been described, e.g. in German Offenlegungsschrift No. 2,263,602 and in British Pat. No. 1,266,655. The layers may also be hardened by the process according to German Offenlegungsschrift No. 2,218,009 to produce photographic materials which are suitable for high temperature processing.

The photographic layers or colour photographic multilayered materials may also be hardened with diazine, triazine or 1,2-dihydroquinoline hardeners as described in British Pat. Nos. 1,195,290; 1,251,091; 1,306,544 and 1,266,655, in French Pat. No. 7,102,716 and in German Patent application P 23 32 317.3. The following are examples of such hardeners; diazine derivatives containing alkyl sulphonyl or aryl sulphonyl groups; derivatives of hydrogenated diazines or triazines e.g. 1,2,5-hexahydrotriazine; fluoro substituted diazine derivatives, e.g. fluoropyrimidine; esters of 2-substituted 1,2-dihydroquinoline- or 1,2-dihydroisoquinoline-N-carboxylic acid. Vinyl sulphonic acid hardeners, carbodiimide hardeners and carbamoyl hardeners are also suitable, e.g. those described in German Offenlegungsschriften Nos. 2,263,602; 2,225,230 and 1,808,685, French Pat. No. 1,491,807, German Pat. No. 872,153 and DDR Pat. No. 7218. Other suitable hardeners have been described, for example, in British Pat. No. 1,268,550.

The stabilizers used according to the invention are preferably added after chemical ripening to the light sensitive silver halide emulsions. They may, of course, also be added to other photographic layers. The concentration of stabilizers in the emulsion may vary within wide limits and depends on the nature of the emulsion and the desired effect. Quantities of from 20 mg to 3 g, in particular from 50 to 2500 mg, per mol of silver halide generally produce the desired effects. Quantities of from 50 to 2500 mg per mol of silver halide are preferably used in black and white emulsions and from 200 to 2500 mg in emulsions which contain colour couplers. The optimum quantity to be added to each emulsion can easily be determined by the usual preliminary experiments.

The stabilizers to be used according to the invention may also be added to one of the baths used for processing the photographic materials, for example a short stop bath or an after treatment bath. They are used in concentrations of from 0.4 to 2 g per liter, preferably from 0.5 to 1.5 g per liter in the baths.

The following examples serve to explain the invention without limiting it to the embodiments given in the examples.

EXAMPLE 1

A silver bromide emulsion containing 14 mol percent of silver chloride and 1 mol percent of silver iodide for producing a copying paper with a hard gradation is prepared in the usual manner with the addition of sodium hexachlororhodinate, ripened to optimum sensitivity with sulphur sensitizers and washed. The ratio of gelatine to silver in the finished emulsion is 3.6:1, the pH 5.7.

The emulsion is sensitized with 25 ml per kg of emulsion of a 0.1% aqueous solution of the optical sensitizer corresponding to the following formula:

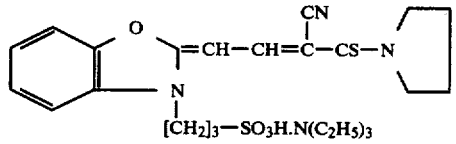

The sensitized emulsion is then divided into several equal parts, and the stabilizers shown in the following table, dissolved in methanol, are added in the given quantities to the individual samples.

Before each sample is cast on a layer substrate of baryta paper, 20 ml of a 5% aqueous solution of saponin and 0.75 ml of a 30% aqueous solution of formaldehyde per kg of emulsion are added to it. The quantity of silver applied, calculated as silver nitrate is 2.7 g of $AgNO_3/m^2$.

A protective layer of the following composition is applied to the emulsion layer:

20 g of gelatine
1 liter of water
2.4 ml of a 30% aqueous formaldehyde solution
7.5 ml of a 5% aqueous saponin solution.

Fresh samples and samples which have been stored for 9 months are exposed behind a $\sqrt[3]{2}$ step wedge at room temperature and developed for 90 seconds at 20° C. in developer 1 which has the composition indicated below. The samples are then fixed and washed in the usual manner.

| Developer I | |
|---|---|
| p-methylaminophenol sulphate | 1 g |
| sodium sulphite sicc. | 13 g |
| hydroquinone | 3 g |
| sodium carbonate sicc. | 26 g |
| potassium bromide | 1 g |

made up with water to 1 liter.

As can be seen from the data summarized in Table 4, excellent stabilization of gradation is achieved in the materials according to the invention, and in most cases a reduction of fogging is also achieved.

The table also gives values for the "long term fog" at high temperature processing. These data are obtained from unexposed materials which have been processed in the same way as the others but have been developed for 2 minutes or 4 minutes at 30° C. instead of for 90 seconds at 20° C. The table shows that some of the materials according to the invention have a substantially lower long term fog than the unstabilized material.

As comparison substance A there is used a conventional stabilizer containing mercapto groups, i.e. p-[3-(2-mercapto-3,4-dihydro-4-ketoquinazolinyl)-benzene sulphonic acid.] This compound has been disclosed as anti-fogging agent in German Offenlegungsschrift No. 1,962,605 and although it acts as an anti-fogging agent, as can be seen from Table 4, it is not capable of stabilizing the sensitivity and the gradation.

TABLE 4

| | | Example 1 Sensitivity: X stage at density 1 | | | | | | | | | |
|---|---|---|---|---|---|---|---|---|---|---|---|
| | | Test on fresh sample | | | | | Re-test after 9 months | | | | |
| | | | | | Long term fog | | | | | Long term fog | |
| Compound | mg/kg | Sensitivity | γ | fog | 2 min. | 4 min. | Sensitivity | γ | fog | 2 min. | 4 min. |
| Control sample | — | 16.9 | 5.1 | 0.06 | 0.08 | 0.18 | 19.1 | 3.7 | 0.06 | 0.10 | 0.20 |
| 1 | 100 | 16.2 | 5.7 | 0.05 | 0.08 | 0.13 | 17.2 | 5.1 | 0.06 | 0.09 | 0.14 |
| 1 | 250 | 16.2 | 6.0 | 0.06 | 0.08 | 0.07 | 16.2 | 5.4 | 0.05 | 0.08 | 0.09 |
| 3 | 217 | 16.2 | 5.3 | 0.06 | 0.07 | 0.11 | 18.5 | 4.2 | 0.07 | 0.07 | 0.10 |
| 4 | 333 | 15.2 | 5.3 | 0.05 | 0.05 | 0.09 | 16.8 | 5.1 | 0.06 | 0.06 | 0.14 |
| 10 | 75 | 16.4 | 5.4 | 0.05 | 0.07 | 0.09 | 16.9 | 5.7 | 0.06 | 0.04 | 0.11 |
| 10 | 149 | 16.2 | 5.4 | 0.05 | 0.05 | 0.07 | 16.5 | 5.1 | 0.06 | 0.05 | 0.08 |
| A | 30 | 16.5 | 5.2 | 0.04 | 0.08 | 0.11 | 18.6 | 3.9 | 0.05 | 0.08 | 0.11 |

EXAMPLE 2

30 g of an alkali soluble yellow coupler corresponding to the following formula:

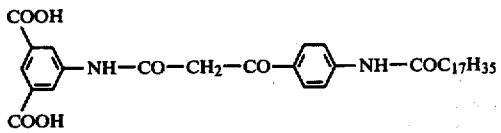

dissolved in aqueous-methanolic sodium hydroxide were added to 1 kg of a blue sensitized silver iodobromide emulsion containing 0.24 mol of silver halide (consisting of silver bromide with a silver iodide content of 1 mol percent). The pH of the emulsion was then adjusted to 6.7, 1 g of saponin dissolved in water was added as wetting agent and in addition there were added 0.2 g of 4-hydroxy-6-methyl-1,3,3a,7-tetraazaindene in aqueous-alkaline solution and 1 g of 1,3,5-triacrylohexahydro-1,3,5-triazine in methanolic solution as hardener. The resulting emulsion was divided into several equal parts and the compounds according to the invention shown in the following table were added to the individual samples in the quantities indicated, which were chosen to leave the sensitive unaffected as far as possible.

The samples of emulsion were cast on corona irradiated polyethylene coated paper in quantities corresponding to a silver application of 0.75 g $AgNO_3/m^2$. The emulsion layer was covered in each case with a 2% gelatine solution to which 0.3 g per liter of 1,3,5-triacrylohexahydro-2,3,5-triazine in methanolic solution had been added. The gelatine solution was applied in a thickness corresponding to 2 g of gelatine/$m^2$.

After drying, the materials were exposed behind a step wedge and developed for 110 seconds at 35° C. in developer II of the following composition:

| Developer II | |
|---|---|
| Trisodium salt of nitrilotriacetic acid | 2 g |
| sodium sulphite sicc. | 3 g |
| potassium bromide | 0.4 g |
| potassium carbonate | 35 g |
| benzyl alcohol | 5 ml |
| hydroxylamine hydrochloride | 3 g |
| N—butyl-N—ω-sulphobutyl-p-phenylene diamine | 6 g |

made up with water to 1 liter.

The materials are then processed in the following baths: Short stop bath: buffer solution of sodium acetate and acetic acid adjusted to pH 6.5. Bleach fixing bath:

10 g of the $Na_4$ salt of ethylene diamino-N,N,N',N'-tetraacetic acid,
2 g of sodium sulphite sicc.,
40 g of the sodium-iron-(III)salt of ethylene diamino-tetraacetic acid,
13 g of disodium phosphate,
100 g of ammonium thiosulphate, made up with water to 1 liter and adjusted to pH 7.2.

The processing times after development are as follows:

| | |
|---|---|
| Short stop bath | 1 minute |
| Washing | 1 minute |
| Bleach fixing | 3 minutes |
| Washing | 3 minutes. |

Yellow images of the step wedge are obtained. To determine the "long term fog," unexposed samples are processed in the same way except that they are developed for 165 seconds.

As the results summarized in Table 5 show, the compounds reduce the colour fog, especially when the development time is prolonged.

Comparison substance B is the anti-fogging agent 2-amino-5-propyn-(2)-ylthio-1,3,4-thiadiazole disclosed in German Offenlegungsschrift No. 2,304,321. Comparison substance B is less effective in reducing the fog, especially the long term fog, than the compounds according to the invention, and it reduces the sensitivity and flattens the gradation even when used as relatively low concentrations.

TABLE 5

| | | Developer II | | | | |
|---|---|---|---|---|---|---|
| Compound number. | mg/kg | Sensitivity* | Gradation | D max | Fog | Long term fog |
| Control Sample | — | 18.5 | 2.54 | 1.75 | 0.22 | 0.28 |
| 1 | 50 | 18.3 | 2.53 | 1.70 | 0.14 | 0.15 |
| 3 | 87 | 18.5 | 2.54 | 1.71 | 0.18 | 0.20 |
| 4 | 333 | 18.4 | 2.54 | 1.76 | 0.14 | 0.24 |
| 5 | 336 | 18.6 | 2.51 | 1.74 | 0.14 | 0.20 |
| 10 | 374 | 18.2 | 2.48 | 1.74 | 0.11 | 0.22 |
| 11 | 154 | 18.2 | 2.53 | 1.73 | 0.17 | 0.16 |
| 12 | 162 | 18.3 | 2.54 | 1.71 | 0.11 | 0.20 |
| 15 | 203 | 18.2 | 2.60 | 1.75 | 0.16 | 0.18 |
| Comparison experiment | | | | | | |
| B | 20 | 18.0 | 2.44 | 1.74 | 0.18 | 0.20 |
| B | 60 | 17.6 | 2.31 | 1.71 | 0.16 | 0.18 |

*Sensitivity = X stage at density 1.

We claim:

1. Light sensitive color photographic material having at least one silver halide emulsion layer, of improved stability and containing grains for formation of an image upon imagewise exposure, and said material having associated with said silver halide layer [a color developer and] color-*forming* compounds and at least one stabilizing compound, wherein the improvement comprises the stabilizing compound of the following general formula or a salt thereof:

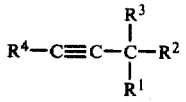

in which $R^1$ represents a substituted or unsubstituted alkyl, aryl, aralkyl, or heterocyclic group, $R^2$ represents a hydroxyl group, or a nitrogen-containing heterocyclic group having 5 or 6 ring atoms.

$R^3$ represents a substituted or unsubstituted aryl group $R^4$ represents hydrogen, a substituted or unsubstituted alkyl, aryl or dialkylamino alkyl group, a morpholinomethyl group or an N-pyrrolidinyl methyl group, provided that at least one of the groups $R^1$ and $R^2$ is a heterocyclic group.

2. Light sensitive photographic material according to claim 1 in which the stabilizer corresponds to the following general formula:

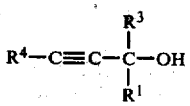

in which $R^1$ represents a nitrogen-containing heterocyclic group, $R^3$ represents a phenyl group which may have one or more substituents and $R^4$ has the meaning specified above.

3. Light sensitive photographic material according to claim 1 in which $R^1$ represents alkyl having 1 to 4 carbon atoms; phenyl or a phenyl group substituted with at least one $CF_3O$, nitro, phenyl, phenoxy or alkyl group or with halogen; or a pyridyl-(4), pyridyl-(3) or pyridyl-(2) group.

4. Light sensitive photographic material according to claim 1 containing as stabilizer, at least one compound corresponding to the following formula:

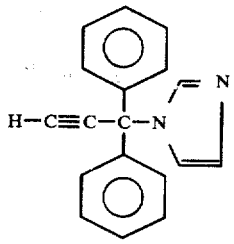

5. Light sensitive material according to claims 1 or 4, containing the stabilizer in a quantity of from 20 to 3000 mg per mol of silver halide.

6. Light sensitive photographic material according to claim 1 containing at least one azaindene stabilizer.

7. Light sensitive color photographic material as claimed in claim 1 wherein $R^2$ represents an imidazolyl-(1) group or a group corresponding to the following general formula:

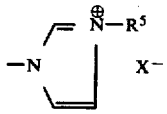

in which $R^5$ represents alkyl, aralkyl or hydrogen and

X represents halogen, alkyl sulphate or aryl sulphate.

8. In a process for the production of color photographic images by imagewise exposure of color photographic material which contains at least one silver halide emulsion layer, having associated therewith [color] *color-forming* compounds and development and stabilization of the silver halide against fog, [the] the improvement according to which development is carried out with a composition containing a developer and at least one compound corresponding to the following formula or a salt thereof:

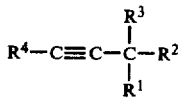

in which $R^1$ represents a substituted or unsubstituted alkyl, aryl, aralkyl, or heterocyclic group, $R^2$ represents a hydroxyl group, or a nitrogen-containing heterocyclic group having 5 or 6 ring atoms[.], $R^3$ represents a substituted or unsubstituted aryl group $R^4$ represents hydrogen, a substituted or unsubstituted alkyl, aryl or dialkylamino alkyl group, a morpholinomethyl group or an N-pyrrolidinyl methyl group, provided that at least one of the groups $R^1$ and $R^2$ is a heterocyclic group.

9. A process for the production of photographic images as claimed in claim 8 wherein $R^2$ represents an imidazolyl-(1) group or a group corresponding to the following formula:

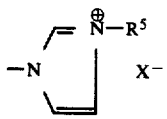

in which $R^5$ represents alkyl, aralkyl or hydrogen and

X represents halogen, alkyl sulphate or aryl sulphate.

* * * * *